US009650338B1

(12) United States Patent
Martirosyan

(10) Patent No.: US 9,650,338 B1
(45) Date of Patent: May 16, 2017

(54) OPIOID ANTAGONIST COMPOUNDS AND METHODS OF MAKING AND USING

(71) Applicant: VDM Biochemicals, Inc., Bedford Heights, OH (US)

(72) Inventor: Vardan Martirosyan, Twinsburg, OH (US)

(73) Assignee: VDM Biochemicals, Inc., Bedford Heights, OH (US)

( * ) Notice: Subject to any disclaimer, the term of this patent is extended or adjusted under 35 U.S.C. 154(b) by 0 days.

(21) Appl. No.: 15/223,187

(22) Filed: Jul. 29, 2016

(51) Int. Cl.
C07D 211/58 (2006.01)
A61K 9/00 (2006.01)
A61K 47/12 (2006.01)

(52) U.S. Cl.
CPC .......... *C07D 211/58* (2013.01); *A61K 9/0019* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 3,923,992 | A | 12/1975 | Riley et al. |
| 4,725,634 | A | 2/1988 | Ishii et al. |
| 5,145,966 | A | 9/1992 | Aumueller et al. |
| 5,635,204 | A | 6/1997 | Gevirtz et al. |
| 5,863,903 | A | 1/1999 | Lundgren et al. |
| 6,024,976 | A | 2/2000 | Miranda et al. |
| 6,284,266 | B1 | 9/2001 | Zhang et al. |
| 6,476,041 | B1 | 11/2002 | Thompson et al. |
| 6,737,527 | B2 | 5/2004 | Haremza et al. |
| 6,903,085 | B1 | 6/2005 | Thom et al. |
| 7,074,935 | B2 | 7/2006 | Mathew et al. |
| 7,390,500 | B2 | 6/2008 | Mueller |
| 7,790,215 | B2 | 9/2010 | Sackler et al. |
| 8,200,327 | B2 | 6/2012 | Southam et al. |
| 8,354,432 | B2 | 1/2013 | Carter et al. |
| 8,449,907 | B2 | 5/2013 | Miller, II et al. |
| 8,486,972 | B2 | 7/2013 | Kottayil et al. |
| 8,501,778 | B2 | 8/2013 | Li et al. |
| 8,563,038 | B2 | 10/2013 | Andersen et al. |
| 8,603,984 | B2 | 12/2013 | Newbound et al. |
| 8,728,441 | B2 | 5/2014 | Eichman et al. |
| 8,742,111 | B1 | 6/2014 | Walz et al. |
| 8,808,740 | B2 | 8/2014 | Huang |
| 8,889,176 | B2 | 11/2014 | Watts et al. |
| 8,987,290 | B2 | 3/2015 | Woodward |
| 9,089,527 | B2 | 7/2015 | Hille et al. |
| 9,226,902 | B2 | 1/2016 | Tang |
| 2002/0106407 | A1 | 8/2002 | Coleman et al. |
| 2004/0092531 | A1* | 5/2004 | Chizh .................. A61K 31/452 514/255.05 |
| 2004/0234584 | A1 | 11/2004 | Muller et al. |
| 2005/0226922 | A1 | 10/2005 | Ameri et al. |
| 2007/0243221 | A1 | 10/2007 | Cavezza et al. |
| 2007/0253924 | A1 | 11/2007 | Cavezza et al. |
| 2007/0265307 | A1 | 11/2007 | Cavezza et al. |

(Continued)

FOREIGN PATENT DOCUMENTS

| | | |
|---|---|---|
| CN | 102617449 A | 8/2012 |
| CN | 103232433 A | 8/2013 |
| CN | 105111136 A | 12/2015 |
| EP | 1980240 A1 | 10/2008 |
| EP | 2039360 A1 | 3/2009 |
| FR | 2983712 A1 | 6/2013 |
| WO | 2004046110 A1 | 6/2004 |
| WO | 2009157586 A1 | 12/2009 |
| WO | 2011047981 A1 | 4/2011 |
| WO | 2014190440 A1 | 12/2014 |
| WO | 2015191554 A1 | 12/2015 |

OTHER PUBLICATIONS

Haghighatnia, et al., "Designing and Synthesis of Novel Amidated Fentanyl Analogs," Helvetica Chimca Acta, v. 95, n. 5, pp. 818-824, published 2012.

(Continued)

*Primary Examiner* — Brian J Davis
(74) *Attorney, Agent, or Firm* — Fernengel Law, LLC

(57) ABSTRACT

The present invention is aimed at providing an opioid antagonist compound and preparation method thereof, and its medical use. The medical use for opioid antagonists such as the compound of formula (I) (shown below) include complete or partial reversal of narcotic depression, including respiratory depression, induced by opioids including natural and synthetic narcotics, such as heroin, fentanyl, oxycodone, hydrocodone, morphine, propoxyphene, methadone and certain narcotic-antagonist analgesics, such as nalbuphine, pentazocine and butorphanol. An opioid antagonist may also be useful as an adjunctive agent to increase blood pressure in the management of septic shock. Further, opioid antagonists also have been shown to reduce the craving for alcohol.

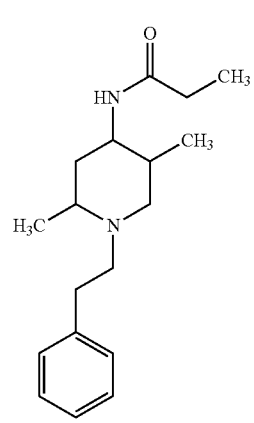

(I)

15 Claims, No Drawings

(56) References Cited

U.S. PATENT DOCUMENTS

| | | |
|---|---|---|
| 2008/0031947 A1 | 2/2008 | Hamed et al. |
| 2008/0090874 A1 | 4/2008 | Messina |
| 2009/0118400 A1 | 5/2009 | Sawaguchi |
| 2010/0080829 A1 | 4/2010 | Dulieu et al. |
| 2010/0168103 A1 | 7/2010 | Pajouhesh et al. |
| 2011/0020426 A1 | 1/2011 | Baird et al. |
| 2011/0111013 A1 | 5/2011 | Salman et al. |
| 2011/0136847 A1 | 6/2011 | Chan et al. |
| 2011/0195520 A1 | 8/2011 | Leider et al. |
| 2011/0257632 A1 | 10/2011 | Castile et al. |
| 2012/0015007 A1 | 1/2012 | Bredenberg et al. |
| 2012/0209223 A1 | 8/2012 | Salman et al. |
| 2013/0273119 A1 | 10/2013 | Engqvist et al. |
| 2014/0005617 A1 | 1/2014 | Choi et al. |
| 2014/0052051 A1 | 2/2014 | Tagliaferri et al. |
| 2014/0243765 A1 | 8/2014 | Yu et al. |
| 2014/0271492 A1 | 9/2014 | Bartley et al. |
| 2014/0271799 A1 | 9/2014 | Venkatraman et al. |
| 2015/0064231 A1 | 3/2015 | Li |
| 2015/0218180 A1 | 8/2015 | McCrathy et al. |
| 2015/0250733 A1 | 9/2015 | Odidi |
| 2015/0283087 A1 | 10/2015 | Vamvakas et al. |
| 2016/0001957 A1 | 1/2016 | Bradway et al. |

OTHER PUBLICATIONS

Weltrowska, et al., ""Carba"-Analogues of Fentanyl are Opioid Receptor Agonists," J. Med. Chem., v. 53, n. 7, pp. 2875-2881, published 2010.

Jimeno, et al., "Fentanyl and Its Analogue N-(1-Phenylpyrazol-3-yl)-N-[1-(2-phenylethyl)-4-piperidyl]propanamide: 1H- and 13C-NMR Spectroscopy, X-Ray Crystallography, and Theoretical Calculations," Chem. Pharm. Bull. 51(8), pp. 929-934, published 2003.

Finney, et al., "4-Anilidopiperidine Analgesics. 3. 1-Substituted 4-(Propananilido) perhydroazepines as Ring-Expanded Analogues," J. Med. Chem., v. 23, n. 8, pp. 895-899, published 1980.

Jagerovic, et al., "Long-Acting Fentanyl Analogues: Synthesis and Pharmacology of N-(1-Phenylpyrazolyl)-N-(1-phenylalkyl-4-piperidyl)propanamides," Bioorganic & Medicinal Chemistry, v. 10, n. 3, pp. 817-827, published 2002.

Dardonville, et al., "Antiprotozoal Activity of 1-Phenethyl-4-Aminopiperidine Derivatives," Antimicrobial Agents and Chemotherapy, pp. 3815-3821, v. 53, n. 9, published 2009.

Lau, et al., "A convenient large-scale chiral synthesis of protected 2-substituted 4-oxo-piperidine derivatives," Tetrahedron, v. 58, n. 36, pp. 7339-7344, published 2002.

Katritzky, et al., "Preparation of polysubstituted piperidines via radical cyclization," J. Med. Chem., Perkin Transactions 2, n. 7, pp. 1375-1380, published 2000.

Van Bever, et al., "N-4-Substituted 1-(2-Arylethyl)-4-piperidinyl-N-phenylpropanamides, a Novel Series of Extremely Potent Analgesics with Unusually High Safety Margin," Arzneim.-Forsch. (Drug Res.), v. 26, n. 8, pp. 1548-1551, published 1976).

Van Daele, et al., "Synthetic Analgesics: N-(1-[2-Arylethyl]-4-substituted 4-Piperidinyl) N-Arylalkanamides," Arzneim.-Forsch. (Drug Res.), v. 26, n. 8, pp. 1521-1531, published 1976).

Ragoussi, et al., "Stereoselective Synthesis of 2,4,5-Trisubstituted Piperidines via Radical Cyclization," J. Org. Chem., v. 75, n. 21, pp. 7347-7357, published 2010.

\* cited by examiner

OPIOID ANTAGONIST COMPOUNDS AND METHODS OF MAKING AND USING

FIELD OF THE INVENTION

The present invention relates to the field of pharmaceutical chemistry and particularly relates to an opioid antagonist compound and methods for the preparation thereof.

BACKGROUND OF THE INVENTION

Opioid antagonist compounds have been approved by the FDA for some time for the complete or partial reversal of opioid intoxication. For example, naloxone was approved by the FDA in 1971 and first marketed as Narcan® injection for the complete or partial reversal of opioid intoxication. It has subsequently become a multisource prescription generic drug available in two strengths, 0.4 mg/mL and 1.0 mg/mL.

At present, naloxone is utilized by emergency services personnel for reversal of suspected opioid overdose. Hospital emergency departments carry this medication for the same purpose. Naloxone is also indicated as a reversal agent when the effects of therapeutic use of opioids are no longer medically necessary.

According to the Centers for Disease Control and Prevention, in 2008, poisoning became the leading cause of injury death in the United States. Nearly 9 out of 10 poisoning deaths are caused by drugs. During the past three decades, drug poisoning deaths increased by six fold, from about 6,100 in 1980 to about 36,500 in 2008. Between 1999 and 2008, the number of drug poisoning deaths involving opioid analgesics more than tripled from about 4,000 to about 14,800. In 2008, opioid analgesics were involved in more than 40% of drug poisonings, whereas in 1999, opioid analgesics were involved in 25% of drug poisoning.

Due to the increasing need for opioid overdose reversal agents, there is a need in the art for new and alternate compositions. Although naloxone is generally effective for opioid reversal, as with any medication, there are people who do not react well to naloxone. An alternative medication would be useful. The instant disclosure seeks to address one or more of these unmet needs.

SUMMARY OF THE INVENTION

The present invention provides an opioid antagonist compound, methods for the preparation thereof, and its medical use. The medical use for opioid antagonist compounds such as the compound of formula (I) (shown below) include complete or partial reversal of narcotic depression, including respiratory depression, induced by opioids including natural and synthetic narcotics, such as heroin, fentanyl, morphine, oxycodone, hydrocodone, propoxyphene, methadone and certain narcotic-antagonist analgesics, such as nalbuphine, pentazocine and butorphanol. An opioid antagonist compound may also be useful as an adjunctive agent to increase blood pressure in the management of septic shock. Further, opioid antagonist compounds also have been shown to reduce the craving for alcohol.

An exemplary embodiment of such a compound that provides a technical solution to the above problems is an opioid antagonist compound comprising a pharmaceutical composition represented by formula (I), an enantiomer, a diastereoisomer and a racemate thereof, and a pharmaceutically acceptable salt or solvate thereof:

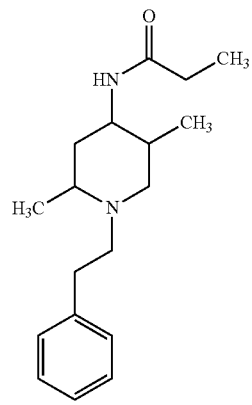

(I)

In the opioid antagonist compound of the present invention, the term "pharmaceutically acceptable salt" means a compound represented by formula (I) in salt form that retains at least a portion of, and in certain instances, all of the therapeutic efficacy and nontoxicity of the non-salt form. In certain exemplary embodiments, a salt is formed by contacting a compound of formula (I) with an acid. Examples of such acids include inorganic acids, for example, hydrochloric acid, sulfuric acid, nitric acid, phosphoric acid and the like; or organic acids such as acetic acid, trifluoroacetic acid, propionic acid, glycolic acid, 2-hydroxy propionic acid, 2-oxopropionic acid, oxalic acid, malonic acid, succinic acid, maleic acid, fumaric acid, malic acid, tartaric acid, 2-hydroxy-1,2,3-tricarballylic acid, methyl sulfonic acid, ethyl sulfonic acid, benzene sulfonic acid, 4-methyl benzene sulfonic acid, cyclohexyl sulfinic acids, 2-hydroxy benzoic acid, 4-amino-2-hydroxy benzoic acid, and so on. These salts are well known by the skilled person in the art. In addition, certain salts may be preferred over other salts based on factors, such as solubility, stability, ease of preparation, etc.

An exemplary method for preparing the compound of formula (I) is as follows:

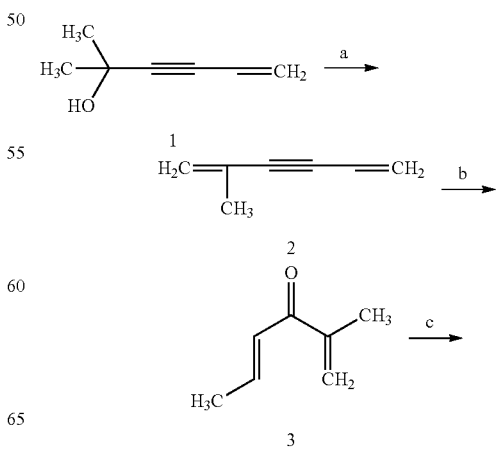

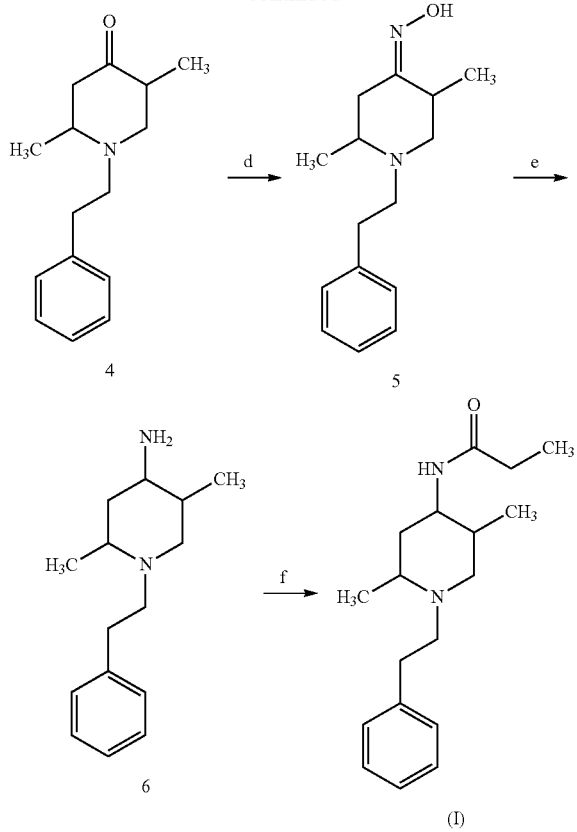

a) H₂SO₄
b) CH₃OH, H₂O, HgSO₄
c) NH₂(CH₂)₂C₆H₅
d) H₂NOH.HCl
e) LiAlH₄, THF, H₂O, NaOH, and MgSO₄
f) triethylamine; C₃H₅ClO The opioid antagonist compound of the present invention can be used for complete or partial reversal of narcotic depression, including respiratory depression, induced by opioids including natural and synthetic narcotics, such as heroin, fentanyl, morphine, oxycodone, hydrocodone, propoxyphene, and methadone, and certain narcotic-antagonist analgesics, such as nalbuphine, pentazocine and butorphanol. The opioid antagonist of the present invention can be useful as an adjunctive agent to increase blood pressure in the management of septic shock. The opioid antagonists also can be used to treat alcoholics by reducing the craving for alcohol.

DETAILED DESCRIPTION OF THE INVENTION

For clarity and consistency, the following definitions will be used herein.

The term "active ingredient" or "pharmaceutically active compound" is defined in the context of a "pharmaceutical composition" and is intended to mean a component of a pharmaceutical composition that provides the primary pharmacological effect, as opposed to an "inactive ingredient" which would generally be recognized as providing little or no pharmaceutical benefit apart from, for example, formulation or delivery.

The term "agonist," as used herein, refers to a moiety that interacts with and activates a receptor, and thereby initiates a physiological or pharmacological response characteristic of that receptor. The term "antagonist," as used herein, refers to a moiety that competitively binds to a receptor at the same site as an agonist, but which does not activate the intracellular response initiated by the active form of the receptor and can thereby inhibit the intracellular responses by an agonist or partial agonist. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist.

The term "naloxone," as used herein, refers to a compound of the following structure:

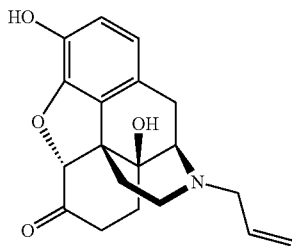

Other names for naloxone include: 17-allyl-4,5a-epoxy-3,14-dihydroxymorphinan-6-one; (−)-17-allyl-4,5a-epoxy-3,14-dihydroxymorphinan-6-one; 4,5a-epoxy-3,14-dihydroxy-17-(2-propenyl)morphinan-6-one; and (−)-12-allyl-7,7a,8,9-tetrahydro-3,7a-dihydroxy-4aH-8,9c-iminoethanophenanthro[4,5-bcd]furan-5(6H)-one.

The term "opioid intoxication," as used herein, refers to an acute medical condition induced by use of one or more opioids. The term "opioid overdose," as used herein, refers to an acute medical condition induced by excessive use of one or more opioids. Symptoms of opioid intoxication and opioid overdose include respiratory depression (including postoperative opioid respiratory depression, acute lung injury, and aspiration pneumonia), central nervous system depression (which may include sedation, altered level consciousness, miotic (constricted) pupils), and cardiovascular depression (which may include hypoxemia and hypotension). Visible signs of opioid intoxication, opioid overdose or suspected opioid overdose include: unresponsiveness and/or loss of consciousness; slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose or quantify, or both, particularly by a lay person, as used herein, treatment of opioid overdose includes treatment of suspected opioid overdose in opioid-intoxicated patients. Opioids that cause opioid intoxication and may induce opioid overdose include, codeine, morphine, methadone, fentanyl, oxycodone.HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol.

The term "pharmaceutical composition," as used herein, refers to a composition comprising at least one active ingredient; including but not limited to its enantiomers, diastereomers, racemates, salts, solvates and hydrates, whereby the composition is amenable to use for a specified, efficacious outcome in a mammal (for example, without limitation, a human).

Opioid Antagonist Compounds

Opioid receptor antagonist compounds are a well recognized class of chemical agents. They have been described in detail in the scientific and patent literature. Opioid antagonist compounds, such as naloxone and the compound of formula (I) of the present invention, namely, N[2,5-dimethyl-1-(2-phenylethyl)piperidin-4-yl]propanamide or 2,5-Dimethyl-1-(2-phenyl)ethyl-4-propionilaminopiperidin, are agents which specifically reverse the effects of opioid agonist compounds but have no opioid agonist activity. Naltrexone is an opioid antagonist compound that is also a partial inverse agonist compound. Structures of Naltrexone and Naloxone are below.

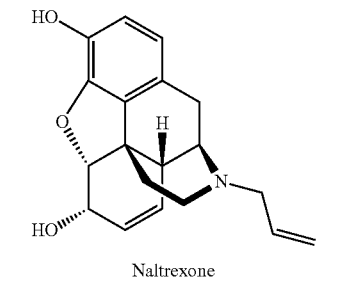

Naltrexone

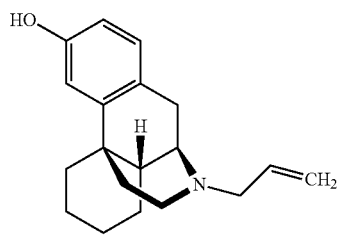

Naloxone

There are also known opioid receptor antagonist compounds that are also partial opioid receptor agonist compounds. Examples include Nalorphine and Levallorphan.

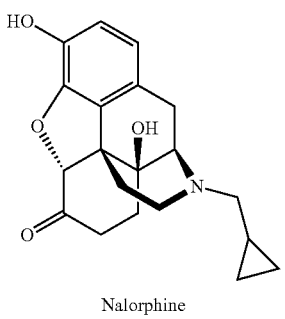

Nalorphine

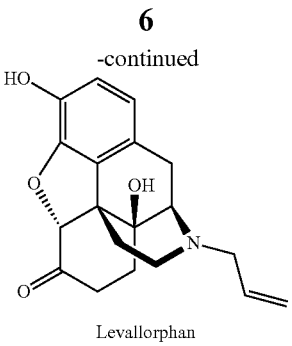

Levallorphan

The structure of the known opioid receptor antagonist compounds and the opioid antagonist/partial agonist compounds all share the same basic structure. One of ordinary skill in the art would not expect a compound lacking the fused ring central structure of the compounds above to show opioid antagonist activity. However, it was surprisingly discovered that the pharmaceutical composition of formula (I) displayed such activity.

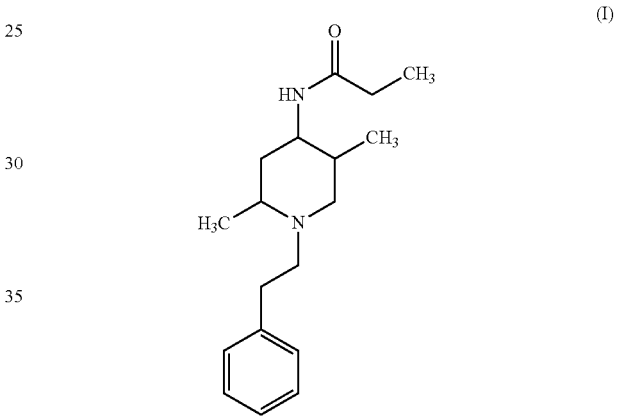

(I)

The pharmaceutical composition of formula (I) is also known as 1-(2-phenylethyl)-2,5-dimethyl-4-propionilaminopiperidin or N-[2,5-dimethyl-1-(2-phenylethyl)piperidin-4-yl]propanamide or 2,5-Dimethyl-1-(2-phenyl)ethyl-4-propionilaminopiperidin. The pharmaceutical composition of formula (I) functions as an opioid receptor antagonist compound, even though it is quite different in structure to known opioid antagonist compounds. In fact, the pharmaceutical composition of formula (I) of the present invention actually more closely resembles an opioid agonist, fentanyl, shown below:

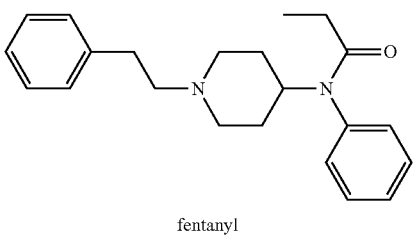 [SMILES: CCC(=O)N(c1ccccc1)C1CCN(CCc2ccccc2)CC1]

fentanyl

Fentanyl, in stark contrast to the pharmaceutical composition of formula (I), is a potent opioid agonist compound. In other words, it is the functional opposite of the inventive pharmaceutical composition of formula (I). Fentanyl is a potent analgesic that has historically been used to treat breakthrough pain. The abuse of fentanyl has led to many opioid overdoses, which are actually treated by opioid antagonist compounds such as the pharmaceutical composition of formula (I). Considering that the structure of the pharmaceutical composition of formula (I) much more closely resembles a known powerful opioid agonist than the known opioid antagonists, it was a surprising discovery that the inventive compound of formula (I) functions as an opioid receptor antagonist. According to the CDC, Fentanyl is estimated to be 80 times as potent as morphine and hundreds of times more potent than heroin.

The inventive pharmaceutical composition of formula (I) fills the need of a new opioid antagonist compound to help treat opioid overdose, along with other uses associated with opioid antagonist compounds.

The invention relates to a pharmaceutical composition for the treatment of individuals with medical conditions that may benefit from the use of an opioid antagonist compound such as the pharmaceutical composition of formula (I).

This invention also relates to a method of treating opioid intoxication, opioid overdose, or suspected opioid overdose, in an individual in need, comprising administering to said individual an amount of the compound of formula (1) that is effective in treating said opioid intoxication, opioid overdoes or suspected opioid overdose. The opioid intoxication or opioid overdose is treated by complete or partial reversal of narcotic depression, including respiratory depression induced by opioids including natural and synthetic narcotics, propoxyphene, methadone, fentanyl, heroin or any similar narcotic. The narcotic depression may also be induced by narcotic-antagonist analgesic compounds such as nalbuphine, pentazocine, butorphanol, or similar analgesic medication.

This invention also relates to a method of treating septic shock in an individual in need, comprising administering to said individual an amount of the pharmaceutical composition of formula (I) that is effective in treating septic shock. The pharmaceutical composition of formula (I) may increase blood pressure in the treatment of septic shock.

This invention also relates to a method of treating alcoholism in an individual in need, comprising administering to said individual an amount of the pharmaceutical composition of formula (I) that is effective in treating alcoholism. The pharmaceutical composition of formula (I) may reduce cravings for alcohol, thereby treating alcoholism.

The effects of the inventive pharmaceutical composition of formula (I) have been compared to naloxone and are set forth below. Tables 1-3 show the Antagonist Activity as the $AD_{50}$ (Median Effective Dose for Anticiception) in mg/kg of the composition of formula (I) as compared to naloxone. The parenthetical number shows the ranges. Although the dose of the pharmaceutical composition of formula (I) required to reach $AD_{50}$ is higher than naloxone, it is effective as an alternative and, correspondingly, solves a long-felt need for an alternative to naloxone.

TABLE 1

The effect of the inventive pharmaceutical composition of formula (I) vs. naloxone on the analgesic effects of the $ED_{99}$ of morphine (rat, under skin injection, model by mechanical irritation of the tail, morphine in 5 mg/kg dosage)

| Compound | Median Antagonistic activity $AD_{50}$ mg/kg (parenthetical is range) |
|---|---|
| naloxone | 0.3 (0.22-0.39) |
| pharmaceutical composition of formula (I) | 1.2 (0.8-1.64) |

TABLE 2

The effect of the inventive pharmaceutical composition of formula (I) vs. naloxone on the cloudiness caused by the $ED_{99}$ of Fentanyl on the lens of the eye (mouse, intraperitoneal administration, Fentanyl in 3 mg/kg dosage)

| Compound | Median Antagonistic activity $AD_{50}$ mg/kg (parenthetical is range) |
|---|---|
| naloxone | 0.08 (0.043-0.120) |
| pharmaceutical composition of formula (I) | 0.11(0.08-0.160) |

TABLE 3

The effect of the pharmaceutical composition of formula (I) vs. naloxone on the respiratory depression caused by $LD_{50}$ of Promedol (rat, Promedol (Trimeperidine) in 70 mg/kg dosage)

| Compound | Median Antagonistic activity $AD_{50}$ mg/kg (parenthetical is range) |
|---|---|
| naloxone | 1.8 (1.1-3.2) |
| pharmaceutical composition of formula (I) | 5.1 (3.4-7.8) |

Tables 4 and 5 show the affinity of composition of formula (I) to the opiate receptor sites is superior as compared to naloxone. The affinity of a drug for a receptor is a measure of how strongly that drug binds to the receptor. In particular, Table 4 shows the competitive binding of the pharmaceutical composition of formula (I) to the opiate receptor site in the brain of a rat compared to naloxone. The affinity $IC_{50}$ (nM) is more than three times greater for the inventive pharmaceutical composition of formula (I) than for naloxone. Table 5 shows that the competitive binding of the inventive compound is superior to naloxone as well. This higher affinity for the pharmaceutical composition of formula (I) than naloxone is an advantage over the known compound of naloxone.

TABLE 4

The competitive binding of the inventive
pharmaceutical composition of
formula (I) to the opiate receptor sites in
the CNS (brain of the rat, $^3$H- Naloxone)

| Compound | Affinity IC$_{50}$(nM) |
| --- | --- |
| naloxone | 0.41 |
| pharmaceutical composition of formula (I) | 0.12 |

TABLE 5

The competitive binding of the inventive
pharmaceutical composition of formula (I)
to the opiate receptor sites in the CNS M$^+$m Investigating IC$_{50}$ nm

| Object | Naloxone | | Compound of formula (I) | |
| --- | --- | --- | --- | --- |
| Brain of the mouse | 0.3 | 0.06 | 0.1 | 0.05 |
| Brain of the rate | 0.41 | 0.11 | 0.12 | 0.05 |

The invention also relates to an injectable pharmaceutical composition comprising the pharmaceutical composition of formula (I) or a pharmaceutically acceptable salt thereof and a pH adjustor. In one embodiment, the composition contains about 1 mg to about 100 mg of the compound of formula (I) and about 1 mg to about 100 mg of a pH adjustor. In another embodiment, the composition contains about 10 mg of the compound of formula (I) and about 10 mg of a pH adjustor. In still another embodiment, the pH adjustor is citric acid. In an alternative embodiment, any pH adjustor known to be safe and effective for use in injectable pharmaceutical products for the adjustment of pH may be utilized.

The following examples are served to exemplify the present invention, but not to limit the scope of the invention.

The first example provides a process for the preparation of Vinilisopropenilacetilen (2) from Dimethyl(vinyl)ethynylcarbinol (1). The second example provides a process for the preparation of Preparation of 2-Methyl-hexan-1,4-dien-3-one (3) from Vinilisopropenilacetilen (2). The third examples provides a process for the preparation of 1-(2-phenyletyl-2,5-dimethyl-4-piperidone (4) from 2-Methyl-hexan-1,4-dien-3-one (3). The fourth examples provides a process for the preparation of Oxym 1-(2-phenylethyl)-2,5-dimethyl-piperidin-4-one (5) from 1-(2-phenyletyl-2,5-dimethyl-4-piperidone (4). The fifth examples provides a process for the preparation of 1-(2-phenylethyl)-2,5-dimethyl-4-amino piperidin (6) from Oxym 1-(2-phenylethyl)-2,5-dimethyl-piperidin-4-one (5). The sixth examples provides a process for the preparation of the compound of formula (I) from 1-(2-phenylethyl)-2,5-dimethyl-4-amino piperidin (6). The examples can be followed sequentially from Example 1 through Example 6 to produce the compound of formula (I) from the starting material of Dimethyl(vinyl)ethynylcarbinol (1).

Example 1: Preparation of Vinilisopropenilacetilen (2) from Dimethyl(Vinyl)Ethynylcarbinol (1)

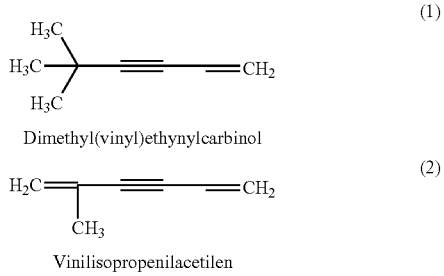

Dimethyl(vinyl)ethynylcarbinol

Vinilisopropenilacetilen

A stirred solution of 100 G 50% H$_2$SO$_4$ was cooled to 10° C. To this solution was added dropwise 100 G of Dimethyl (vinyl)ethynylcarbinol (1) over 30 minutes. The reaction mixture was then stirred for 4 hours at 60-65° C., after which the reaction mixture was cooled. The organic phase was separated from the reaction mixture and purified by vacuum distillation at 70-75° C. (20 mm) to give 80 G (73%) of Vinilisopropenilacetilen (2).

Example 2: Preparation of 2-Methyl-hexan-1,4-dien-3-one (3) from Vinilisopropenilacetilen (2)

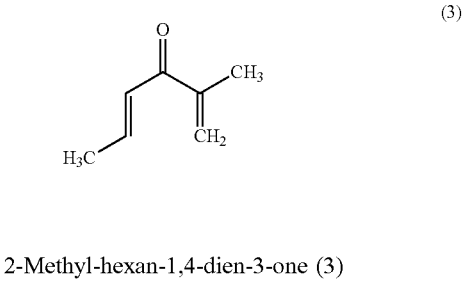

2-Methyl-hexan-1,4-dien-3-one (3)

73 G (0.79 mol) of Vinilisopropenilacetilen (2), as prepared in Example 1, was mixed with 200 ml of methanol and 30 ml of 5% H$_2$SO$_4$ at 60-65° C. The mixture was then added to 3 G HgSO$_4$. The solution was stirred at 60-65° C. for 5 hours. The mixture was then allowed to stir at room temperature for an additional 3 hours. Saturated NaHCO$_3$ solution was added. The methanol was then evaporated by vacuum. The resulting residue was extracted with EtOAc, washed with water, dried using Na$_2$SO$_4$, and concentrated. The crude residue was purified by vacuum distillation at 90-95° C. (7 mm) to give 79 G (91%) of 2-Methyl-hexan-1,4-dien-3-one (3).

Example 3: Preparation of 1-(2-phenyletyl-2,5-dimethyl-4-piperidone (4) from 2-Methyl-hexan-1,4-dien-3-one (3)

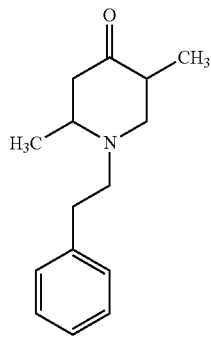

1-(2-phenyletyl-2,5-dimethyl-4-piperidone (4)

79 G (0.72 mol) of 2-Methyl-hexan-1,4-dien-3-one (3), as prepared in Example 2, was mixed with 200 ml methanol and was cooled to 10-15° C. To this solution was added dropwise 87 G (0.72 mol) of phenylethyl amine over 45 minutes. The reaction mixture was stirred for 18 hours at room temperature. The methanol was then evaporated in vacuum. The crude product was purified by column chromatography on silica gel (eluting with EtOAc/Hexane) to give 65 G of the compound of 1-(2-phenyletyl-2,5-dimethyl-4-piperidone (4) (yield 39%). The melting point will be between about 79-80° C.

Example 4: Preparation of Oxym 1-(2-phenylethyl)-2,5-dimethyl-piperidin-4-one (5) from 1-(2-phenyletyl-2,5-dimethyl-4-piperidone (4)

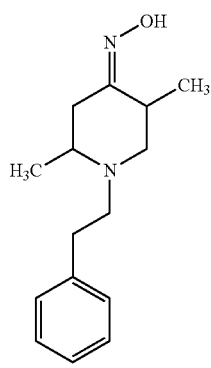

Oxym 1-(2-phenylethyl)-2,5-dimethyl-piperidin-4-one (5)

4.6 G (0.02 mol) of 1-(2-phenyletyl-2,5-dimethyl-4-piperidone (4), as prepared in Example 3, is mixed with 25 ml ethanol to form a solution. The solution was then added a solution of 4.0 G (0.06 mol) hydroxylamine hydrochloride and 6.0 G sodium acetate in 15 ml water. The mixture was then stirred at room temperature for 2 hours. The crystals obtained were filtered off and dried to give 4.2 G of the compound of Oxym 1-(2-phenylethyl)-2,5-dimethyl-piperidin-4-one (5) (yield 85%). The melting point will be between about 101-102° C.

Example 5: Preparation of 1-(2-phenylethyl)-2,5-dimethyl-4-amino piperidin (6) from Oxym 1-(2-phenylethyl)-2,5-dimethyl-piperidin-4-one (5)

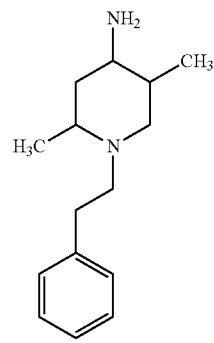

1-(2-phenylethyl)-2,5-dimethyl-4-amino piperidin (6)

To a suspension of 0.76 G (0.02 mol) LiAlH$_4$ in 50 mL tetrahydrofuran at 0° C. was added a solution of 2.46 G (0.01 mol) of Oxym 1-(2-phenylethyl)-2,5-dimethyl-piperidin-4-one (5), as prepared in Example 4, in 20 mL tetrahydrofuran over 45 minutes. The mixture was then allowed to warm to room temperature and stirred for 3 hours. The mixture was then cooled to 0° C. and the reaction was quenched by the addition of water (25 ml), 1M sodium hydroxide (10 ml) and silica gel (10 G). The granular precipitate was filtered off through a pad of Celite. The filtrate was dried using MgSO$_4$ and concentrated in vacuum. The crude product was purified by vacuum distillation at 165-168° C. (2 mm) to give 1.5 G of 1-(2-phenylethyl)-2,5-dimethyl-4-amino piperidin (6) (yield 65%).

Example 6: Preparation of compound of formula (I) from 1-(2-phenylethyl)-2,5-dimethyl-4-amino piperidin (6)

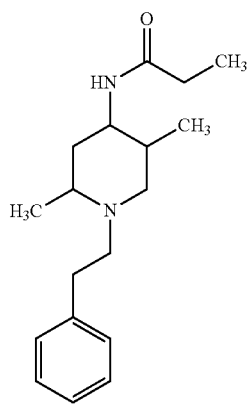

1.5 G (0.0065 mol) 1-(2-phenylethyl)-2,5-dimethyl-4-amino piperidin (6), as prepared in Example 5, was mixed with 2 mL of triethyl amine in anhydrous CH$_2$Cl$_2$ 35 ml and was then stirred for 30 minutes at room temperature. The reaction mixture was cooled to 0° C. and 0.644 G (0.007 mol) propionyl chloride was then added dropwise over 15 minutes. The reaction mixture was allowed to warm to room temperature and stirred for another 2 hours and then evaporated to dryness. The residue was washed thoroughly with water and re-dissolved in CHCl$_3$. The solution was dried with anhydrous Na$_2$SO$_4$, then filtered, and then evaporated to dryness. The crude product was purified by column chromatography on silica gel (eluting with EtOAc/Hexane) to give 1.2 G of the compound of formula (I) as white solid (Yield 64%). The melting point was about 152-153° C.

Although the present disclosure has been described with reference to specific embodiments, it should be understood that the limitations of the described embodiments are provided merely for purpose of illustration and are not intended to limit the present invention and associated general inventive concepts. Instead, the scope of the present invention is defined by the appended claims, and all variations and equivalents that fall within the range of the claims are intended to be embraced therein. Other embodiments than the specific exemplary ones described herein are equally possible within the scope of these appended claims. Therefore, the present invention, in its broader aspects, is not limited to the specific details, the representative compounds, and illustrative examples shown and described herein as departures may be made from such details without departing from the spirit or scope of the applicant's general inventive concept.

What is claimed is:

1. An opioid antagonist compound comprising a pharmaceutical composition represented by formula (I):

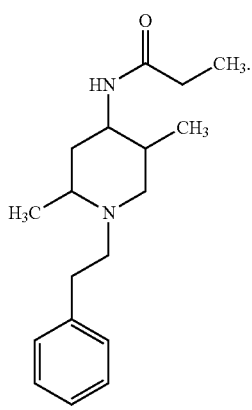
(I)

2. A method of preparing an opioid antagonist compound represented by formula (I), the method comprises:
  mixing the compound of formula 6 with triethylamine in anhydrous CH$_2$Cl$_2$; adding propionyl chloride; and dissolving in CHCl$_3$ to yield the compound of formula (I):

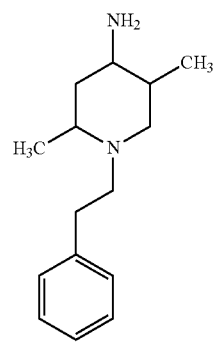
(6)

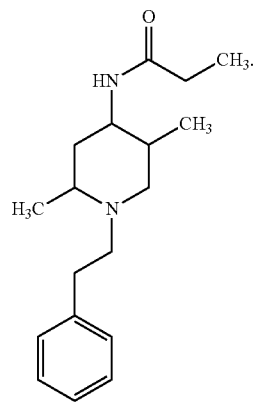
(I)

3. A method of preparing the opioid antagonist compound according to claim 1, the method comprising reacting compound (1) with H$_2$SO$_4$ to provide compound (2); reacting compound (2) with CH$_3$OH, H$_2$SO$_4$, H$_2$O, and HgSO$_4$ to provide compound (3); reacting compound (3) with NH$_2$(CH$_2$)$_2$C$_6$H$_5$ to provide compound (4); reacting compound (4) with H$_2$NOH.HCl to provide compound (5); reacting compound (5) with LiAlH$_4$, THF, H$_2$O, NaOH, and MgSO$_4$ to provide compound (6); reacting compound (6) with triethylamine, CH$_2$Cl$_2$, C$_3$H$_5$ClO, CHCl$_3$, and Na$_2$SO$_4$ to provide the compound of formula (I); synthesis route thereof is as follows:

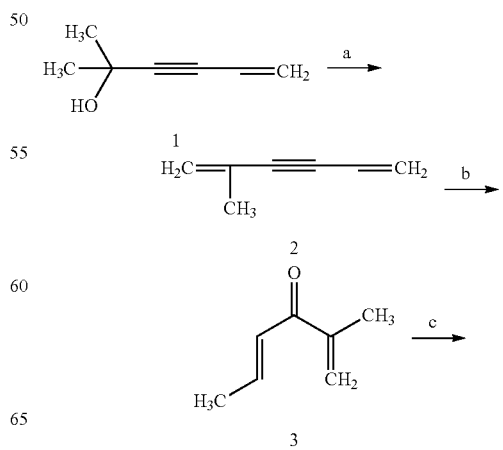

-continued

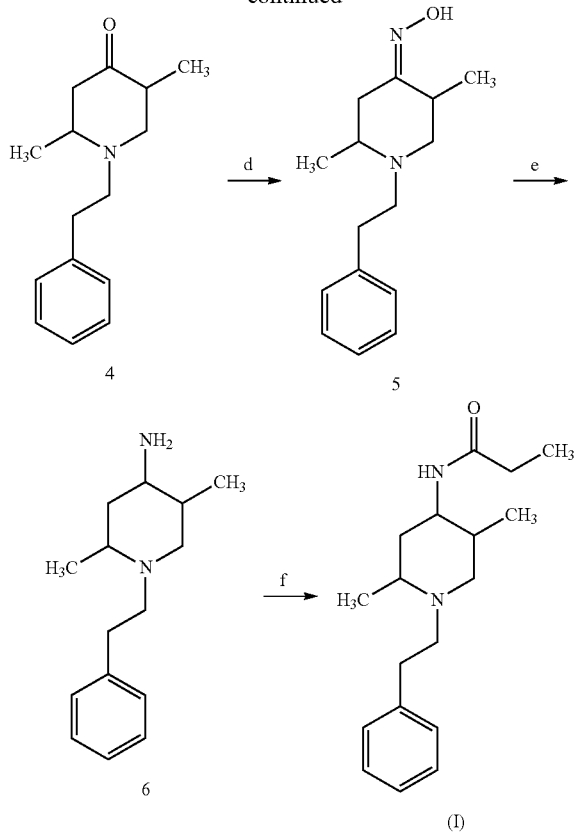

a) $H_2SO_4$
b) $CH_3OH$, $H_2SO_4$, $H_2O$, and $HgSO_4$
c) $NH_2(CH_2)_2C_6H_5$
d) $H_2NOH \cdot HCl$
e) $LiAlH_4$, THF, $H_2O$, NaOH, and $MgSO_4$
f) triethylamine, $CH_2Cl_2$, $C_3H_5ClO$, $CHCl_3$, and $Na_2SO_4$.

4. A pharmaceutical composition for the treatment of opioid intoxication, septic shock, or alcoholism comprising an amount of the compound of claim 1 that is effective in the treatment of said opioid intoxication, septic shock, or alcoholism.

5. A method for the treatment of opioid intoxication comprising administering an effective amount of the compound claim 1 to an individual in need thereof.

6. The method according to claim 5, wherein the opioid intoxication was induced by an opioid agonist compound.

7. The method according to claim 5, wherein the opioid intoxication was induced by a narcotic-antagonist analgesic compound.

8. The method according to claim 5, wherein the opioid intoxication is an opioid overdose.

9. A method for the treatment of septic shock comprising administering an effective amount of the compound of claim 1 to an individual in need thereof.

10. A method for the treatment of alcoholism comprising administering an effective amount of the compound of claim 1 to an individual in need thereof.

11. An injectable pharmaceutical composition comprising:
(a) 1-(2-phenylethyl)-2,5-dimethyl-4-propionil aminopiperidin or a pharmaceutically acceptable salt thereof, and
(b) a pH adjustor.

12. The pharmaceutical composition according to claim 11, wherein the composition comprises:
(a) about 1 mg to about 100 mg of 1-(2-phenylethyl)-2,5-dimethyl-4-propionil aminopiperidin or a pharmaceutically acceptable salt thereof, and
(b) about 1 mg to about 100 mg of the pH adjustor.

13. The pharmaceutical composition of claim 12, wherein the 1-(2-phenylethyl)-2,5-dimethyl-4-propionil aminopiperidin or a pharmaceutically acceptable salt thereof is present in an amount of about 10 mg.

14. The pharmaceutical composition of claim 12, wherein the pH adjustor is citric acid.

15. The pharmaceutical composition of claim 14, wherein the citric acid is present in an amount of about 10 mg.

* * * * *